US00PP22346P2

(12) United States Plant Patent
Smith et al.

(10) Patent No.: US PP22,346 P2
(45) Date of Patent: Dec. 13, 2011

(54) ***HELENIUM* PLANT NAMED 'TIJUANA BRASS'**

(50) Latin Name: *Helenium autumnale*
Varietal Denomination: Tijuana Brass

(76) Inventors: Michael Vern Smith, Scappoose, OR (US); Maurice R. Horn, Portland, OR (US)

( * ) Notice: Subject to any disclaimer, the term of this patent is extended or adjusted under 35 U.S.C. 154(b) by 2 days.

(21) Appl. No.: 12/925,571

(22) Filed: Oct. 25, 2010

(51) Int. Cl.
*A01H 5/00* (2006.01)
(52) U.S. Cl. ..... Plt./435
(58) Field of Classification Search ..... Plt./435
See application file for complete search history.

*Primary Examiner* — Kent L Bell
(74) *Attorney, Agent, or Firm* — Penny J. Aguirre

(57) ABSTRACT

A new cultivar of hybrid *Helenium*, 'Tijuana Brass', characterized by its long season of bloom, it upright growth habit that resists lodging, its clean foliage that persists on the lower portions of the stems, its flowers that are larger in size than most *Helenium*, and its hardiness in U.S.D.A. Zones 4 to 8.

2 Drawing Sheets

Botanical classification: *Helenium autumnale.*
Variety denomination: 'Tijuana Brass'.

BACKGROUND OF THE INVENTION

The present invention relates to a new and distinct cultivar of *Helenium autumnale* and will be referred to hereafter by its cultivar name, 'Tijuana Brass'. 'Tijuana Brass' represents a new *Helenium*, an herbaceous perennial grown for landscape use.

The Inventor discovered the new *Helenium* as an open pollinated seedling of *Helenium autumale* 'Kugelsonne' (not patented) in a nursery block in Scappoose, Oreg. in 2003 where it was flagged for further evaluation.

Asexual reproduction of the new cultivar was first accomplished by division by the Inventor in Scappoose, Oreg. in late winter of 2006. The characteristics of this cultivar have been determined to be stable and are reproduced true to type in successive generations.

SUMMARY OF THE INVENTION

The following traits have been repeatedly observed and represent the characteristics of the new cultivar. These attributes in combination distinguish 'Tijuana Brass' from other cultivars of *Helenium* known to the Inventor.

1. 'Tijuana Brass' exhibits an upright growth habit with strong stems resistant to lodging.
2. 'Tijuana Brass' exhibits a vigorous growth habit producing numerous flower stems.
3. 'Tijuana Brass' exhibits flowers that are larger than most *Helenium.*
4. 'Tijuana Brass' exhibits foliage that is disease resistant and persists on the lower stems throughout the bloom sequence of the plant.
5. 'Tijuana Brass' has a long period of bloom.
6. 'Tijuana Brass' is readily propagated by division and tissue culture.
7. 'Tijuana Brass' is reliably hardy in U.S.D.A. Zones 4 to 8.

The new cultivar differs from its parent plant, 'Kugelsonne', by exhibiting a more upright growth habit, exhibiting more vigor, producing more flowers, producing flowers of a different shade of yellow, and maintaining foliage on the lower stems throughout the blooming season. 'Tijuana Brass' may also be compared to 'Zimbelstern' (not patented). 'Tijuana Brass' has similar colored inflorescences, however 'Tijuana Brass' exhibits a taller plant habit, produces inflorescences that are larger in size and brighter in color, has central disk florets that are less brown in color, and maintains its foliage on the stems throughout the flowering period.

BRIEF DESCRIPTION OF THE DRAWING

The accompanying colored photographs illustrate the overall appearance and distinct characteristics of the new *Helenium*. The plants in the accompanying photographs were taken of a two year-old plant of 'Tijuana Brass' as grown in a garden in Scappoose, Oreg.

The photograph in FIG. 1 depicts a plant of 'Tijuana Brass' in peak bloom.

Figure 1:
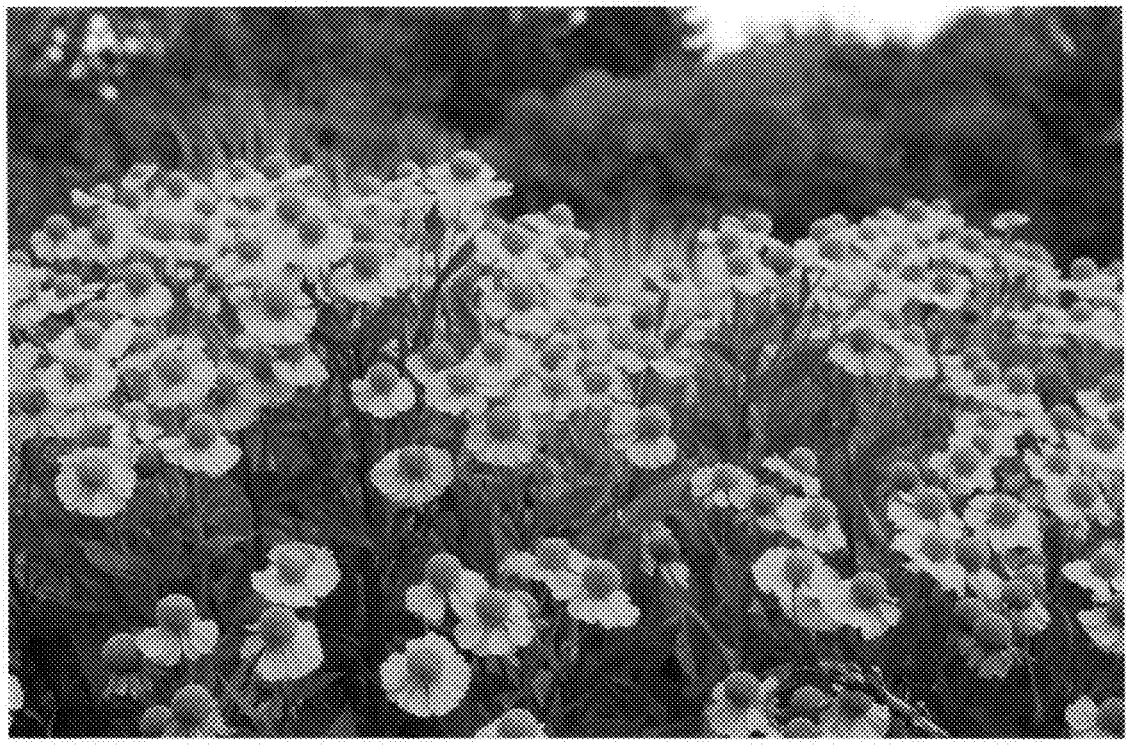
Figure 2:
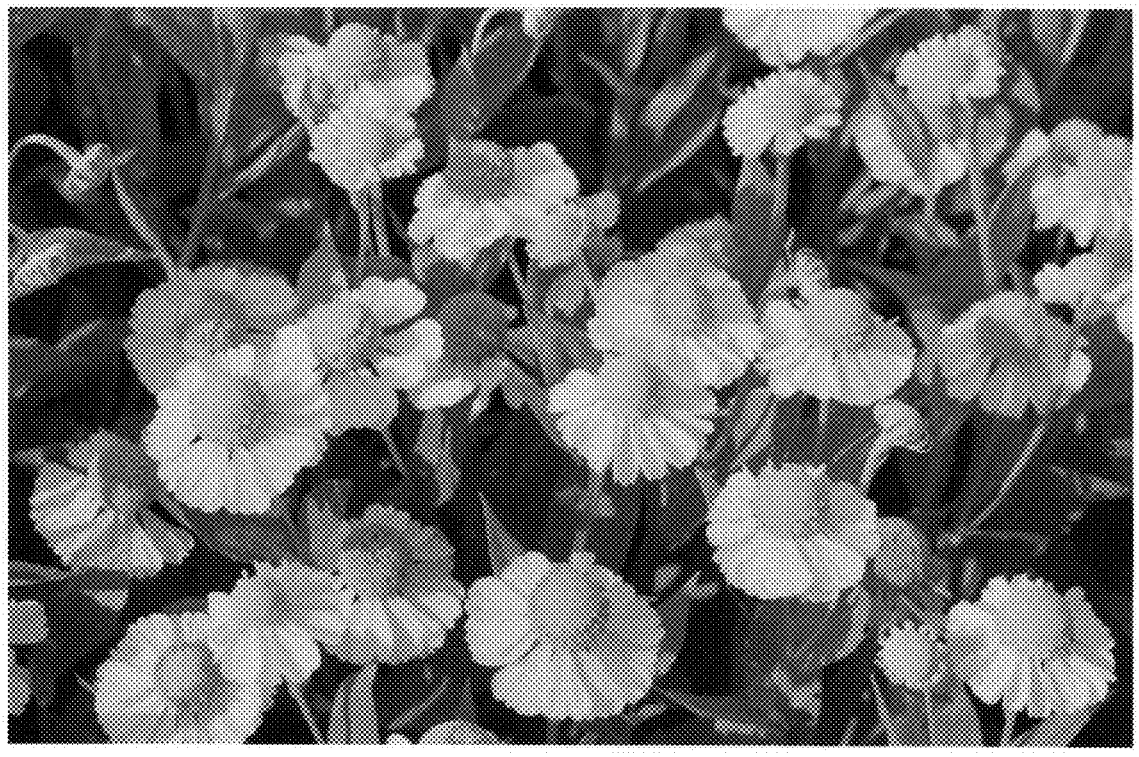

The photograph in FIG. 2 shows a close-up of the inflorescences of 'Tijuana Brass'. The Colors in the photograph may differ slightly from the color values cited in the detailed botanical description, which accurately describe the colors of the new *Helenium.*

BOTANICAL DESCRIPTION OF THE PLANT

The following is a detailed description of one-year-old plants of the new cultivar as grown in a garden in Scappoose, Oreg. The main stems of the plants were pruned to 55 cm in spring. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—Late summer into fall (August 15 to September 30 in Oregon).

*Plant habit.*—Herbaceous perennial, clump forming, upright, freely branched with pruning.

*Height and spread.*—Reaches 1.2 m to 1.5 m in height and about 59 cm in spread.

*Hardiness.*—U.S.D.A. Zones 4 to 8.

*Diseases and pests.*—No susceptibility or resistance to diseases or pests has been observed.

*Root description.*—Fibrous.

Growth and propagation:

*Propagation.*—Division, tissue culture is also possible.

*Growth rate.*—Vigorous.

Stem description:

*Shape.*—Slightly oval.

*Stem color.*—Main stem; a blend of 144C and 144D with ridges of leaf scars N199B, lateral stems; a blend of 144B and 144C with leafy edges a color between 147A and 146A.

*Stem size.*—Main stem; pruned back in spring to an average of 55 cm in length, an average of 1.2 cm in diameter, lateral branches; and an average of 55 cm in length and 6 mm in width, tertiary branches; an average of 14 cm in length and 3.5 cm in length.

*Stem surface.*—Main stem; glabrous, semi glossy with lower region ridged with leaf scars from excurrent leaves, lateral stems; covered with base of leaves with leaf edges extending about 3 mm outward from stem.

*Stem number and branching.*—Pruning of main stems results in an average of 5 lateral stems per main stem and an average of 5 tertiary stems per lateral stem.

*Internode length.*—An average of 3 cm with branching commencing about 32 cm from base of main stem.

Foliage description:

*Leaf shape.*—Oblanceolate.

*Leaf division.*—Simple.

*Leaf base.*—Excurrent to stem with blade truncate to stem.

*Leaf apex.*—Acuminate.

*Leaf venation.*—Pinnate, only mid rib on upper and lower surfaces are conspicuous, color of midrib upper surface 145C, color of mid rib lower surface a blend of 145A and 145B.

*Leaf margins.*—Finely serrulate.

*Leaf attachment.*—Excurrent.

*Leaf arrangement.*—Alternate.

*Leaf size.*—Matures to an average of 11 cm in length and 4 cm in width with leaf base extending an average of 6 cm in next lower node on same side.

*Leaf internode length.*—An average of 3.5 cm.

*Leaf color.*—Newly formed and mature, upper surface; a blend of 147A and 146A, newly formed and mature lower surface; a blend of 147A and 147B.

*Leaf surface.*—Dull and finely puberulent on upper and lower surface.

*Stipules.*—Present at some junctions of the leave blade, same characteristics as stem leaves and an average of 2 cm in length and 8 mm in width.

Inflorescence description:

*Type.*—Capitulum, heterogamous with ray florets around the head margin and disk florets in the center, forming a radiant head.

*Capitulum number.*—1 to 3 capitulums per terminal stem, an average of 32 capitulums per each main stem.

*Lastingness of inflorescence.*—About 10 days until senescence of ray florets, disk florets are persistent.

*Capitulum size.*—About 2.6 cm in depth and 4.6 cm in diameter, disk size is about 1.8 mm in depth and 2.2 cm in diameter.

*Fragrance.*—Lightly fragrant.

*Involucral bracts or phyllary.*—About 40 arranged in 3 overlapping rows, up to 8 mm in length and 2 mm in width, fused at base, acute apex, lanceolate in shape, 137A to 137B in color, entire ciliate margin and glabrous on both surfaces.

*Buds.*—Globose, up to 1.5 cm in diameter and 1 cm in height, phyllary are 144C in color, ray florets are 13A with disk flowers appearing 151A in color when viewed in mass just prior to opening.

*Peduncle.*—Strong, held upright to stem, an average of 5 cm in length and an average of 2 mm in diameter widening to about 3.5 mm at base of capitulum, 146A in color, pubescent surface.

*Ray florets (pistillate).*—About 14, obovate-obdeltoid in shape, vertical ridges on both surfaces, about 2.5 cm in length and 1.4 cm in width, emarginated apex, attenuate base, entire margin except apex, pubescent on upper surface and glabrous on lower surface, initially held upright about 70° from horizontal and become horizontal, then downward as they mature, color of upper and lower surface when opening and fully open; 14A, color of upper and lower when past peak; a blend of 14A and 17A, not persistent.

*Disk florets (bisexual).*—Numerous, about 300, tubular in shape, arranged spirally on a globose receptacle to form a sphere, overall collective color changes from N144A to 17A with the outer region turning first, florets; about 7 mm in length and 1.2 mm in width, phyllaries (5) are fused into tube about 6 mm in length and 1.7 mm in width and 17B at apex and 145C in color near base, translucent.

Reproductive organs:

*Gynoecium.*—Pistil; 1, present on ray and disk florets, 7 mm in length, style; 6 mm in length, 12C in color, surrounded by stamens, stigma; bifid, each arm is reflexed, about 1.5 mm in length and 12B in color, ovary; inferior, 1.5 mm in depth and pubescent, 145D in color.

*Androcoecium.*—Stamens; 5, fused, form a cylinder around style, about 3 mm in length and 0.7 mm in width, filaments are 1C in color, stamens about N199C in color, pollen is abundant in quantity and 17A in color.

*Fruit.*—Seed development has not been observed.

It is claimed:

1. A new and distinct cultivar of *Helenium* plant named 'Tijuana Brass' substantially as herein illustrated and described.

* * * * *